(12) United States Patent
Stiles (10) Patent No.: US 6,783,517 B2
(45) Date of Patent: Aug. 31, 2004

(54) HEART MUSCLE IRRIGATION DEVICE, APPLICATOR AND METHOD

(76) Inventor: Frank B. Stiles, Box 3016, 78 Regency Point Drive, Saywood Estates, Truro, NS (CA), B2N 6L1

(*) Notice: Subject to any disclaimer, the term of this patent is extended or adjusted under 35 U.S.C. 154(b) by 65 days.

(21) Appl. No.: 10/319,581

(22) Filed: Dec. 16, 2002

(65) Prior Publication Data

US 2003/0073883 A1 Apr. 17, 2003

Related U.S. Application Data (63) Continuation-in-part of application No. 09/378,723, filed on Aug. 23, 1999, now Pat. No. 6,558,359, which is a continuation-in-part of application No. 09/378,724, filed on Aug. 23, 1999, now Pat. No. 6,074,375, which is a continuation-in-part of application No. 09/965,382, filed on Nov. 6, 1997, which is a continuation-in-part of application No. 08/965,382, filed on Nov. 6, 1996, now abandoned.
(60) Provisional application No. 60/031,254, filed on Nov. 12, 1996.

(51) Int. Cl.[7] ............................................. A61M 25/00
(52) U.S. Cl. ......................................... 604/268; 604/35
(58) Field of Search ............................. 604/35, 39, 43, 604/48, 115, 118, 133, 149, 151, 174, 179, 180, 268, 313; 607/119, 122

(56) References Cited

U.S. PATENT DOCUMENTS

| | | | |
|---|---|---|---|
| 5,098,411 A | * | 3/1992 | Watson et al. .............. 604/268 |
| 5,224,952 A | * | 7/1993 | Deniega et al. ..... 604/184.08 X |
| 5,727,569 A | | 3/1998 | Benetti et al. |
| 5,836,311 A | | 11/1998 | Borst et al. |

* cited by examiner

Primary Examiner—Anhtuan T. Nguyen
(74) Attorney, Agent, or Firm—Robert A. Wilkes; Shapiro Cohen (57) ABSTRACT

A heart muscle irrigation device comprises a short rivet like member with one closed and one open end, and a barrel including a plurality of holes, slots, an area mesh, or a grid. The irrigation device is inserted into the heart muscle so as to provide a channel from, for example, the left ventricle, to provide an adequate oxygenated blood supply to a starved muscle. The irrigation device is inserted from either outside or inside the rib cage by an insertion device. The insertion device comprises a plunger and barrel assembly adapted to contain the irrigation device. The tip of the insertion device includes members adapted to penetrate the heart muscle. If the irrigation device is inserted through an insertion into the rib cage, an applicator comprising a tubular member with a planar tip including a soft elastomeric seal can be used whereby a portion of the heart muscle is held more or less rigidly for the short period during which the irrigation device is inserted. These devices, even when a rib cage insertion is made, do not require either the life support systems or the extensive rib cage damage associated with conventional bypass surgery.

17 Claims, 5 Drawing Sheets

HEART MUSCLE IRRIGATION DEVICE, APPLICATOR AND METHOD

FIELD OF THE INVENTION

This application is a continuation-in-part of application Ser. No. 09/378,723 filed Aug. 23, 1999 now U.S. Pat. No. 6,558,359 which is a continuation-in-part of Ser. No. 08/965,382 filed Nov. 6, 1996 (now abandoned), which is a continuation-in-part of Ser. No. 09/378,724 filed Aug. 23, 1999 (now U.S. Pat. No. 6,074,375 issued Jun. 13, 2000) which is a continuation-in-part of Ser. No. 09/965,382 filed Nov. 6, 1997 which relates to Ser. No. 60/031,254 filed Nov. 12, 1996.

BACKGROUND TO THE INVENTION

This invention relates to a device, and to a method of using the device, to improve blood flow to the heart muscles. When heart muscles are relatively speaking starved of blood, they are also starved of oxygen, which is carried to them by the blood flow. If a condition in which an inadequate blood flow occurs is allowed to continue to exist for any extended period of time, the heart muscles are in danger of rapid and severe damage, to a point which can be, or can become, life threatening. At present, the most often used therapy to alleviate such a condition is by-pass surgery. This procedure involves invasive surgery which poses a significant risk to the patient and is therefore not lightly undertaken.

This invention seeks to provide an alternative procedure whereby a blood flow can be established to the heart muscles directly. This procedure can be applied to the heart as part of cardiac surgery, when the chest cavity has been opened to provide direct access to the heart muscles. Alternatively, this procedure can be applied through the chest wall, between two adjacent ribs, with only one relatively small incision.

In outline, the irrigation device of this invention is somewhat similar to a small, open ended hollow rivet which has openings or perforations in its cylindrical side wall. By using an insertion device that is similar to a hypodermic syringe, the rivet is inserted into the heart muscle so that the closed end is more or less flush with the outside of the muscle, and the open end is located to receive aerated blood. The blood then flows to the heart muscle through the openings in the cylindrical wall.

Thus in a first embodiment this invention provides a heart muscle irrigation device comprising a hollow substantially cylindrical body having a first closed end and a second open end, the first and second ends each also including radially extending head members, and the cylindrical body having a plurality of radially oriented apertures there through, wherein the head members attached to both the first and the second ends are sufficiently flexible to be bent from a radially extending position, to a position substantially in line with the outside surface of the cylindrical hollow body.

In a second broad embodiment this invention comprises an insertion device for the heart irrigation device comprising a barrel having a first to open end and a second end; flexible means attached to the second end which in a first closed position is adapted to penetrate a heart muscle to provide an opening, and which in a second open position allows passage of an irrigation device contained in the barrel; and plunger means inserted through the first open end of the barrel adapted to eject an irrigation device from the barrel and into engagement with an aperture in the heart muscle.

In a third broad embodiment this invention provides a method for improving blood flow to heart muscles comprising; providing an insertion device in the barrel of which a muscle irrigation device has been inserted with its open end toward the second end thereof, the internal diameter of the barrel being sized to accept the irrigation device with its head members bent from a radially extending position; inserting the second end of the insertion device into and through a selected heart muscle; and simultaneously ejecting the irrigation device through the second end of the insertion device, and withdrawing the insertion device, thus locating the irrigation device in the aperture created in the heart muscle by the insertion device.

In a fourth broad embodiment this invention provides a heart muscle insertion device applicator comprising a hollow tubular member having a first end constructed and arranged to be connected to a surgically acceptable source of vacuum; a substantially planar hollow tip portion attached to the other end of the hollow tubular member and in communication therewith; the tip portion being at an angle to the hollow tubular member, and including a foraminous underside; and a soft elastomeric layer attached to the underside of the tip portion including holes in communication with the foramens in the tip underside.

DESCRIPTION OF THE PREFERRED EMBODIMENTS

The invention will now be described with reference to the attached drawings in which.

Figure 1:
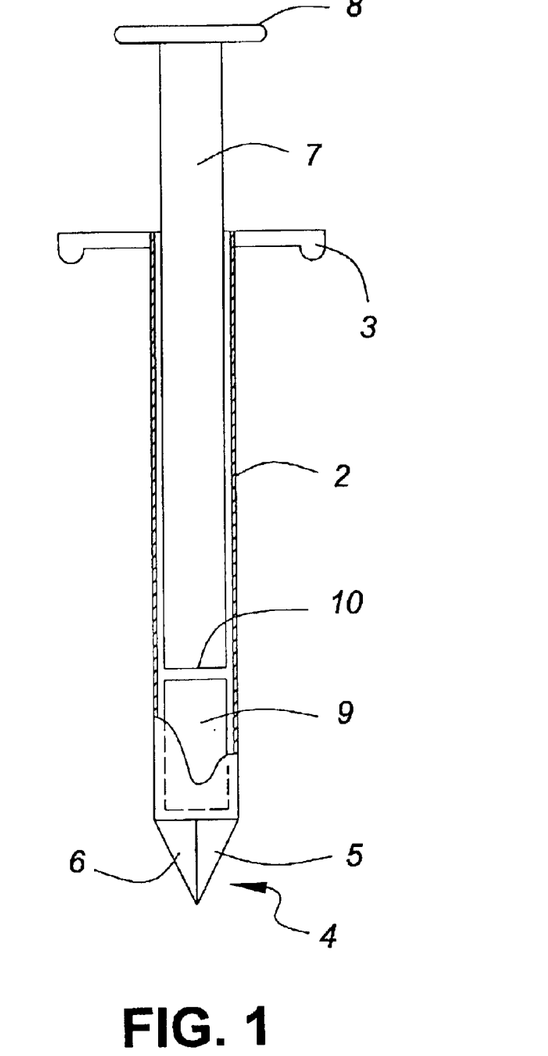
FIG. 1 shows partly sectioned a simple insertion device.

Referring first to FIG. 1, the insertion device 1 is in essentially two parts. The outer barrel 2 is substantially cylindrical, and has attached at, or near, its first open end a pair of finger grips 3. At its second end there is a sharp head 4 which includes a plurality of somewhat petal shaped flexible members 5 and 6. Two such members are shown; in practice four or even six are used. Inside the barrel is a plunger 7, with a head 8. Adjacent the second end of the barrel is the irrigation device, which is also close to the end 10 of the plunger 7.

When used, the head 4 is eased into the heart muscle to form an aperture therein. Its placement into the muscle is carefully monitored by an imaging means, such as a fiber optic imaging system together with an endoscope and other related equipment; suitable devices are well known and readily available. It is inserted until the head 4 has entered a heart chamber or ventricle which contains oxygenated blood. The plunger is then used to eject the irrigation device by deflecting the head parts 5, 6, etc. whilst at the same time slowly withdrawing the insertion device. By coordinating the movement inwardly of the plunger 7, and outwardly of the barrel 2, the irrigation device is left inserted into the aperture made in the heart muscle by the head 4.

Figure 2:
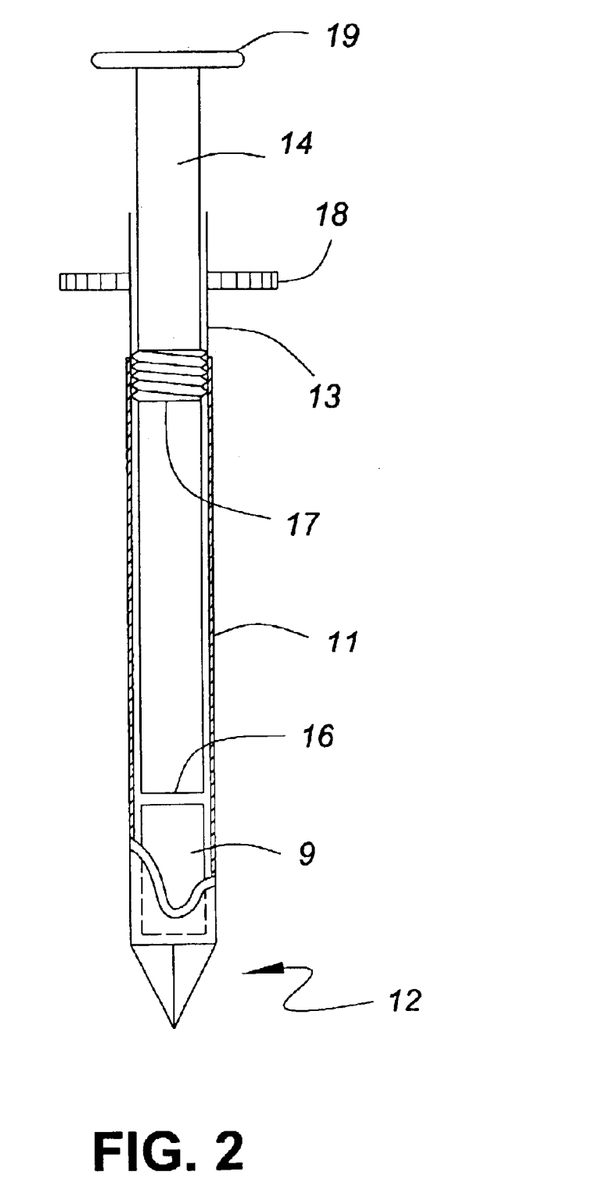
FIG. 2 shows partly sectioned a more complex insertion device.

In FIG. 2 a more sophisticated insertion device is shown. This comprises an outer barrel 11, to which is attached a head unit 12. An inner barrel 13 is a sliding fit into the outer barrel 11. A plunger 14 is fitted inside the inner barrel, as also is the irrigation device 9 adjacent the end 16 of the plunger 14. The plunger is located in the inner barrel by the mating male and female threads shown at 17.

This insertion device is used in more or less the same fashion as that of FIG. 1, but there is more control over the ejection of the irrigation device 9. After the insertion device has been placed through the heart muscle, thus providing the required aperture, the irrigation device is ejected by rotating the turnwheel 18 whilst holding the head 19. As a consequence of the rotation, the plunger 14 is urged by the mating threads 17 toward the irrigation device 9, thus ejecting the irrigation device through the head 12.

Figure 3:
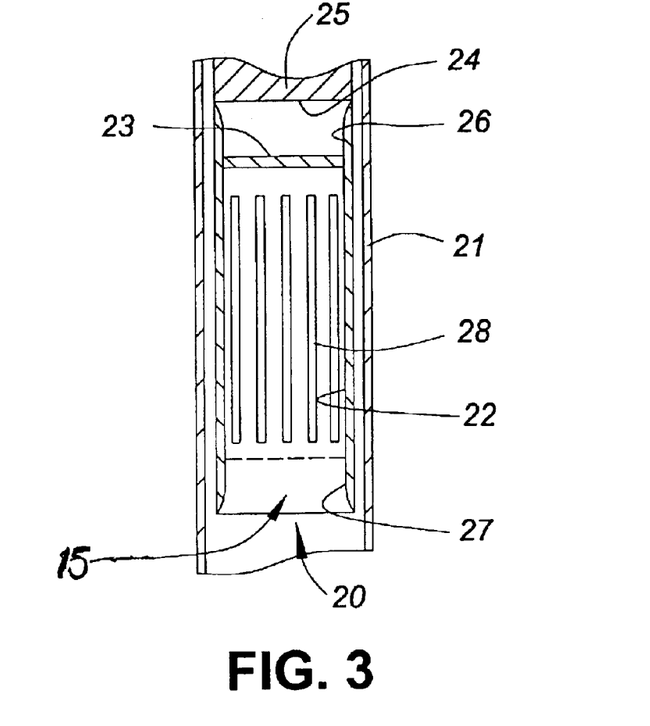
FIG. 3 shows an irrigation device mounted into the barrel of an insertion device.

In FIG. 3 there is shown an irrigation device mounted, ready for use, in a barrel 21. This barrel 21 can be either of those shown in FIG. 1 or 2. The irrigation device 20 includes a cylindrical body portion 22, a first closed end 23, and a second open end 15. The body portion 22 is a sliding fit into the barrel 21. The closed end 23 of the body portion is located adjacent the end 15 of a plunger 25. It can also be seen that when loaded into the insertion device the two radial members 26 and 27 are each bent inwardly from the radial position (see FIG. 4) to be essentially coaxial with the body portion 22, but pointing in opposite directions. This serves to locate the irrigation device in the insertion device whilst it is being assembled, amongst other things. This irrigation device is also provided with a plurality of slots 28 to enable blood to reach the heart muscle tissues from the hollow interior of the body portion 22.

Figure 4:
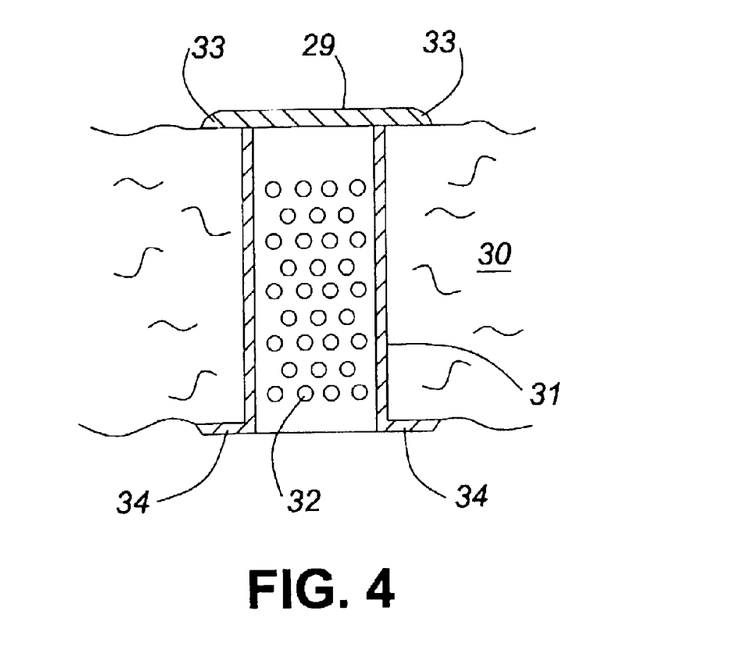
FIG. 4 shows schematically a second irrigation device after placement into a heart muscle.

In FIG. 4 there is shown schematically a different irrigation device 29 lodged into a heart muscle 30. The body portion wall 31 is provided with a plurality of small holes 32 allowing blood access to the tissues of the muscle 30 via the said holes, slots, an area mesh or a grid and hence on into and through the continuously expanding number of collateral blood delivery vessels. As shown a unitary construction is used; a plurality of suitable small holes is also obtainable in a three part construction, in which a portion of the body wall comprises a suitable mesh material. The irrigation device is held in place by the members 33 and 34, which have returned to their essentially radial positions; this happens at each end as the irrigation device is ejected from the barrel.

It is preferred that the irrigation devices as shown in FIGS. 3 and 4 should be coated on at least the inner surface with a material which will at least diminish the possibility of the adherence of substances in the blood flow to the irrigation device. One suitable substance for this purpose is polytetrafluoroethylene, also known as PTFE; other suitable substances are well known.

Whilst the injection device can be used on its own, and indeed would be so used in emergency situations, it is advantageous to be able to hold the heart muscle more or less rigid whilst the irrigation device is being placed. A suitable applicator is shown in FIGS. 5–9.

Figure 5:
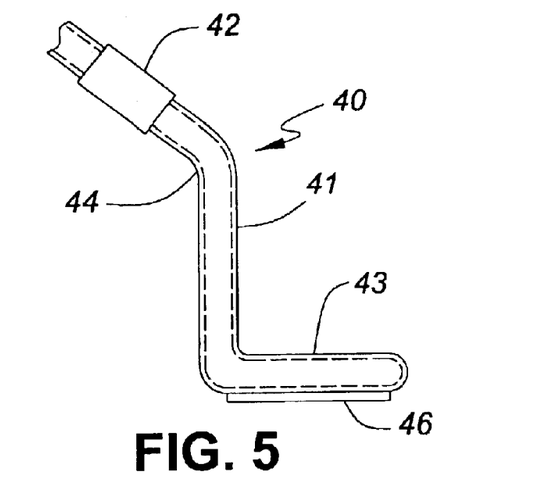
FIG. 5 shows a side view of an applicator for use with the insertion devices of FIGS. 1 and 2.

Referring first to FIG. 5, applicator 40 has a hollow shaft 41 which conveniently has a soft elastomer handle 42. One end of the hollow shaft is provided with a suitable attachment for a surgical vacuum device (not shown). At the other end of the hollow tube a substantially planar tip face 43 extends from the handle. For ease of use, the tip should be at an angle of about 45° to the axis of the hollow shaft. This angle is not critical, and other angles both higher and lower can be used: the angle facilitates location of the insertion device more or less perpendicular to the heart muscle. The angle can be obtained in any suitable way: the hollow shaft can include a bend as at 44, or, as shown at 45 in FIG. 7, the hollow shaft can be attached to the tip at a suitable angle. The tip is also of tubular construction, and communicates with the hollow shaft. The underside of the tip has a layer of soft elastomeric material 46 attached to it. The construction of the shaft and of the tip is discussed further below in the context of FIG. 10.

Figure 6:
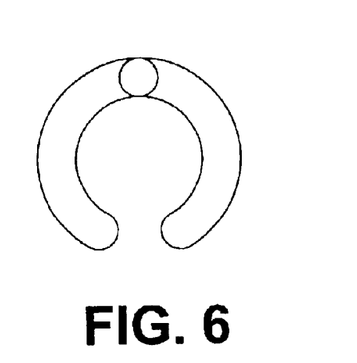
FIGS. 6 and 7 show top views of two end structures for the applicator of FIG. 5.
Figure 7:
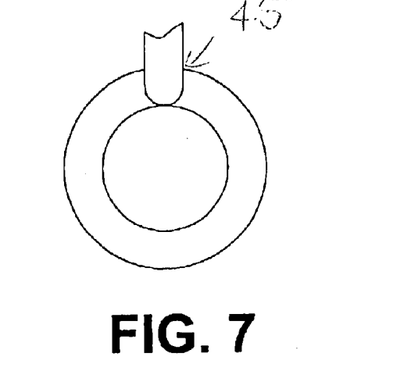

The tip itself as shown in FIGS. 6 and 7 is of more or less circular shape: in FIG. 6 the tip 47 is an arc of a circle which is somewhat like a horseshoe; other suitable shapes are possible. Further, in FIG. 6 the tubular member is shown attached more or less at the centre of the horseshoe as this appears to be the most convenient location; other locations are also possible.

Figure 8:
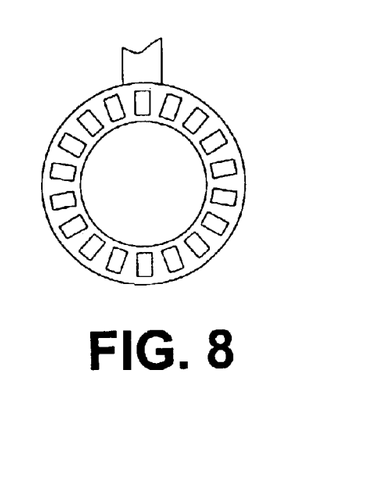
FIGS. 8 and 9 show the construction of the underside of the end structures.
Figure 9:
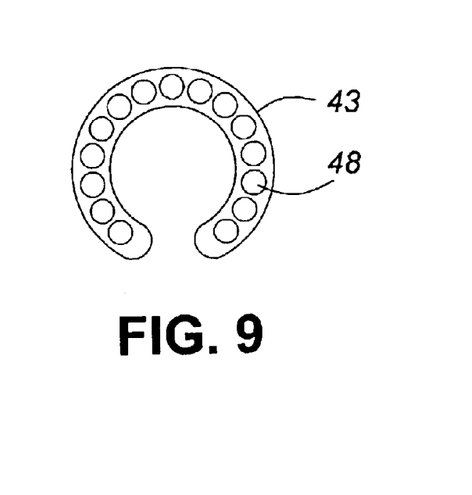

The underside of the tip is foraminous: in FIG. 9 is shown a pattern of holes 48, and in FIG. 8 is shown a series of slots 50. Other arrangements such as in inserted mesh or grid are also possible. In FIGS. 8 and 9 the soft elastomer layer 46 is omitted for clarity. It is either provided with a set of holes to match those in the underside of the tip, or it can, for example, be provided with a slot.

Figure 10:
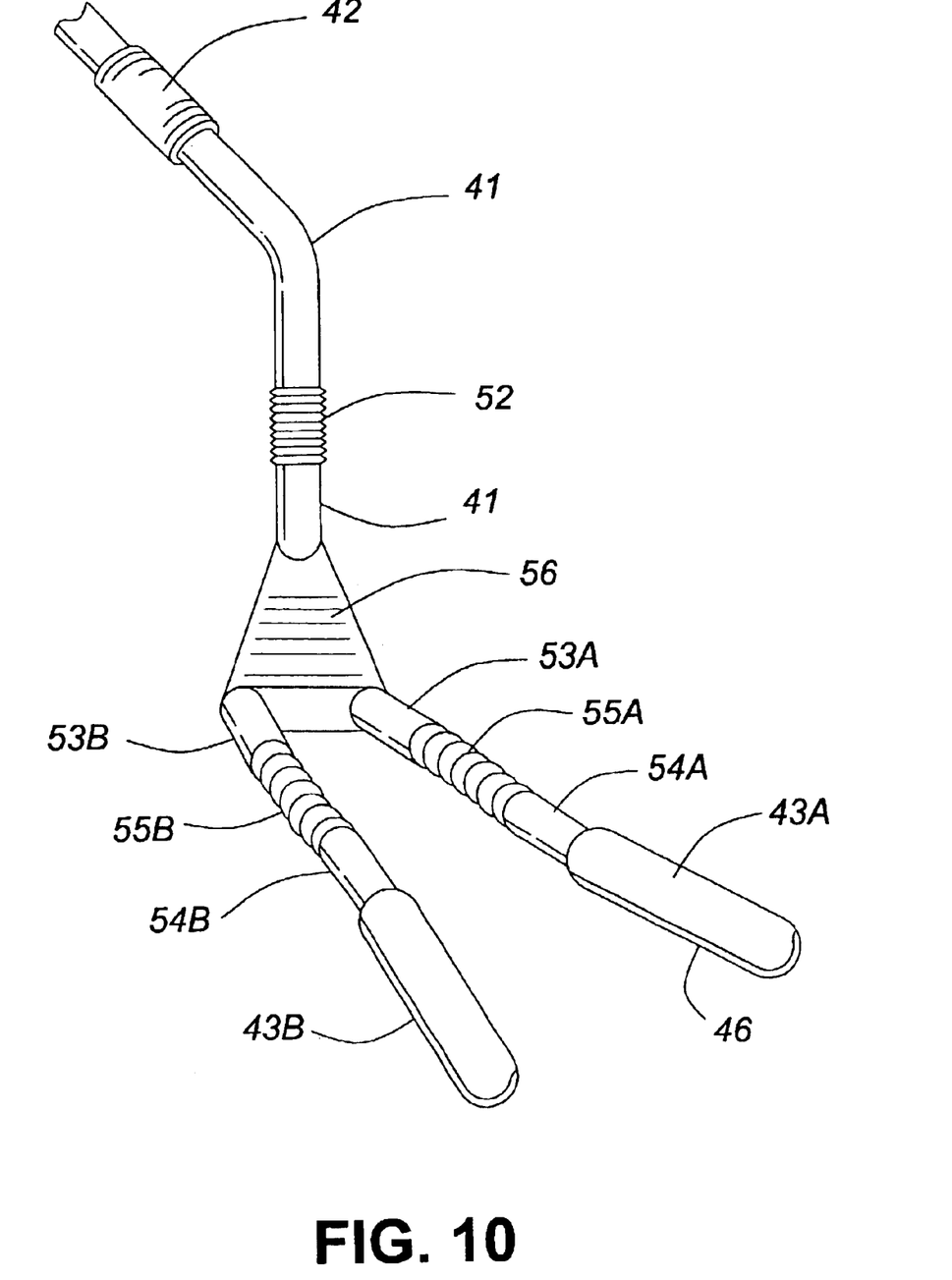
FIG. 10 shows an alternative construction for the applicator.

An alternative construction is shown in FIG. 10. This construction is still based on a vacuum tube 41, which carries a soft elastomer handle 42. Instead of a single tip 43 provided with a soft elastomer layer 46, two separate tips 43A and 43B are provided, each having a soft elastomer layer 46 (the layer for tip 43B is not visible). Each tip is connected to the hollow shaft 41 by a short hollow shaft including a first tubular part 53A, 53B, a flexible part 55A, 55B and a second short tubular part 54A, 54B. The first two tubular parts are both connected into an adapter 56, which is attached to the hollow shaft 41. Additionally, the hollow shaft 41 includes a flexible portion 52. Further, if desired the three joints between the hollow shaft 41 and the two short tubular parts 53A and 53B are constructed so that any or all of them can rotate relative to the adapter 56. Rotatable joints of this type are well known. In FIG. 10 the three flexible parts 52, 55A and 55B are shown as ribbed concertina-like elements: it is also contemplated that each of them can be made by using a material which will provide a tube which is both stiff enough not to collapse under the applied vacuum, and which is flexible enough to be bent into and then retain a desired configuration.

A range of materials are available for the construction of this alternative device. The device can be fabricated as one piece by moulding using a surgically acceptable plastic material, to which. When that procedure is used, the device can be made relatively cheaply and packaged as a sterile single use device. Alternatively, the device can be assembled from more than one piece, each of which need not be the same material. The tube parts may be fabricated from a surgically acceptable metal, such as stainless steel or titanium, and the flexible parts from a suitable plastic. Surgically acceptable plastics materials of this type are well known. The same type of plastics material can also be used for the two tips 43A and 43B, and for the other constructions described above if desired.

In FIG. 10 each tip portion 43A, 43B includes a single internal space in communication with the tubular member

Figure 11:
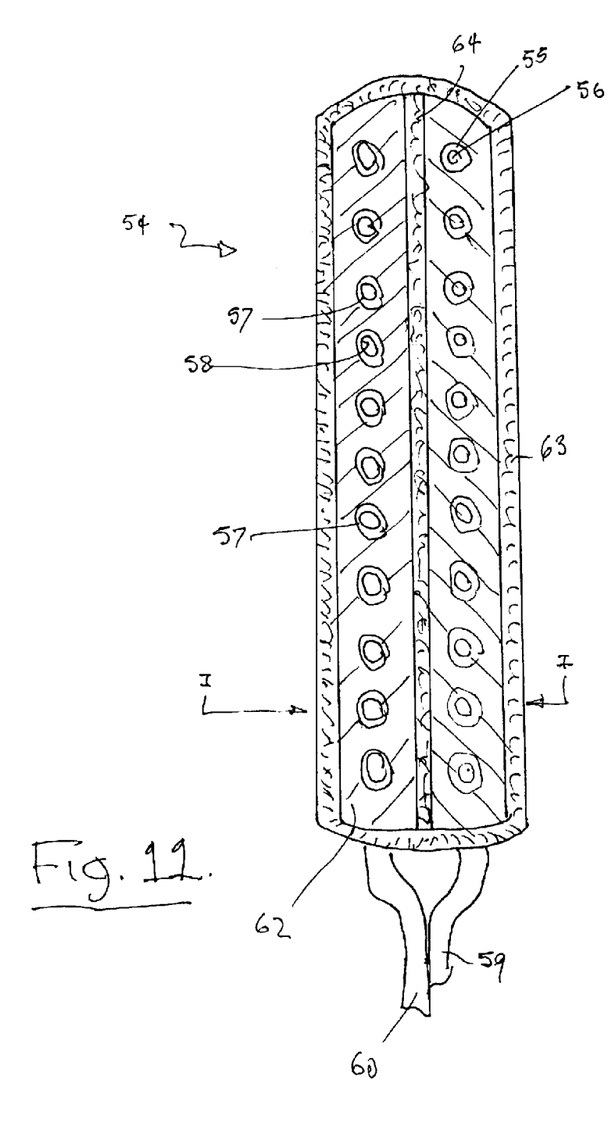
FIG. 11 shows an alternative construction for part of the applicator of FIG. 10.

54A, 54B. If there is a vacuum failure—for whatever reason—the heart muscle stabilising effect is lost. An alternative construction for the underside of the tips is shown in FIG. 11. The top part of the tip portion is much the same shape as shown in FIG. 10.

The underside 54 of the tip portion includes a first set of holes 55 in communication with a first set of foramens 56, and a second set of holes 57 in communication with a second set of foramens 58. The two sets of foramens 56 and 58 each communicate with one of the two spaces provided within the tip portion. The two sets of holes are each surrounded by the soft elastomeric layers 61 and 62. Separate tubular members 59 and 60 are provided each which communicates with only one of the two spaces. Up to this point, the construction of the applicator in FIG. 11 is more or less the same as that in FIG. 10. This construction will provide better stabilisation than that shown in FIG. 10.

The applicator in FIG. 11 includes two further improvements.

First, the outer rim of the underside is provided with an outer wall skirt 63 of soft elastomeric material, which is desirably slightly stiffer than the elastomeric material used for the layers 61 and 62. The wall skirt is also connected to, or made integrally with, an internal more or less central ridge wall 64, made from the same material as the outer wall skirt 63. This construction has the effect of providing two more or less independent spaces to which vacuum can be applied to stabilise the heart muscle. Since each of these spaces is connected by means of the tubular members 59, 60 to two independent vacuum supplies, the risk of losing stabilisation during surgery is significantly reduced. Multiple lumen surgical tubing is well known, and commonly used in the construction of catheters for several purposes.

Figure 12:
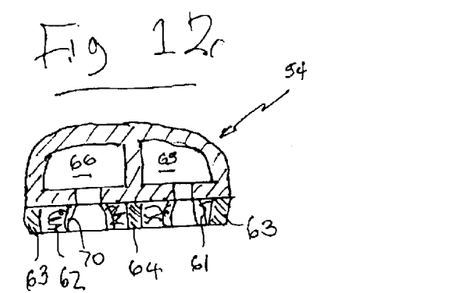
FIG. 12 shows a schematic cross section of the applicator of FIG. 11 on the line I—I.

Second, as is shown in more detail in FIG. 12, which also shows the two separated spaces 65, 66 within the tip portion which communicate with the two tubular members 59, 60, a small preformed flexible suction cup 70 is included in the tip underside in the holes 55, 57 in the elastomeric layers 61, 62. These suction cups, which are of a conventional shape, enhance the seal between the applicator and the heart muscle surface. As shown in FIG. 12, the complete underside surface, including both the suction cups, the wall skirt, and the central ridge wall should be fabricated to have a more or less planar surface for application to the heart muscle surface.

Figure 13:
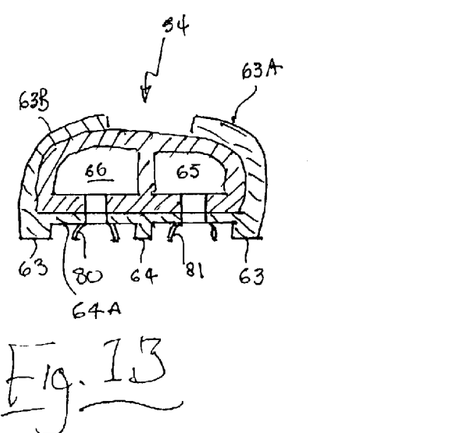
FIG. 13 shows an alternative construction to that shown in FIG. 12.

A further variation is shown in FIG. 13. In FIG. 13 the softer elastomeric parts differ from those of FIG. 12 in three ways. First, two rows of flexible elastomeric independent suction cups as at 80, 81 are used which are attached to an extension of the internal wall 64A which is also attached to the outer wall skirt 63. Second, the layer 62 is omitted. Third, the elastomeric parts are not glued or cemented in place. Instead, the outer wall skirt 63 is continued up the side of the body sufficiently far, as at 63A, 63B, so that the elastomeric parts form a sleeve or shoe which can be conveniently snapped in place over the tip portion. In this construction, a suitable aperture (not shown) will need to be provided for the two tubular members 59, 60. This construction is particularly attractive when the applicator is intended to be reused; only the elastomeric part which has been in contact with a patient's heart and is difficult to sterilise needs to be discarded. As is the case for FIG. 12, the arrangement shown in FIG. 13 also should be fabricated to have a more or less planar surface for application to the heart muscle surface. It is conveniently fabricated as a one piece injection moulding. In either of these constructions, each suction cup is flexible enough to provide a more or less airtight seal to the heart muscle wall.

There are several advantages for the more complex constructions in FIGS. 10, 11, 12 and 13. First, the ability to bend the applicator as a whole allows the surgeon both to place it more accurately and with a better seal to the heart muscle, and to locate the vacuum supply so as not to interfere with the operation. Second, by separating the single tip into two parts the applicator can be used to hold a heart muscle on either side of a heart surface blood vessel, as it will bridge over the blood vessel. Third, by using an applicator with two separate suction surfaces, the risk of losing stabilization during surgery is substantially eliminated. Although it is possible that one vacuum supply might be lost—for example due to pump failure, the loss of two supply sources is most unlikely. Fourth, the presence of two independent rows of suction cups and the outer wall skirt also provide several levels of security against the loss of vacuum. If one or two suction cups in one row become unsealed, those in the other row will take over. If suction cups in both rows become unsealed then the outer wall skirt will provide the required seal. Fifth, the complete applicator can be readily fabricated in several different sizes from surgically acceptable materials.

A range of materials are available for the construction of the applicators shown in FIGS. 10 and 11. The device can be fabricated as one piece by moulding using a suitable surgically acceptable plastic material, to which the elastomeric parts are attached. When that procedure is used, the device can be made relatively cheaply and packaged as a sterile single use device. Alternatively, the device can be assembled from more than one piece, each of which need not be the same material. The tube parts may be fabricated from a surgically acceptable metal, such as stainless steel, titanium, a stiff plastic material such as polyethylene, or a softer fiber reinforced material. Surgically acceptable materials of these broad types are well known. The flexible parts also be made from metal, but it is then necessary that the metal be both thin enough and soft enough to readily bent by a surgeon, and yet also be strong enough not to collapse in use either when bent or under the effects of the applied vacuum. In view of these restrictions, it appears that a plastic material is preferable for the bendable parts, which can then be fabricated much the same as the known bendable drinking straws. The softer elastomeric parts as shown in FIGS. 12 and 13 can be made of any suitable elastomeric material of which several are known. In the construction shown in FIG. 12 the elastomeric parts will be attached using a suitable glue or cement. In the construction shown in FIG. 13 the elastomeric parts can be made as a shoe or sleeve which is sufficiently flexible to be deformed and snapped into place onto the applicator body; this arrangement is particularly suitable when the body of the applicator is fabricated as a multiple use device in a material such as stainless steel or fiber reinforced plastic.

To use the applicator and insertion device together, an insertion is first made in the patient's left rib cage, preferably between the appropriate ribs, for example to provide access to the left heart ventricle muscle. This incision is of an appropriate length, and will generally be not more than 75 mm. in length. An applicator with a vacuum supply attached is then applied to the surface of the heart muscle, so that sufficient vacuum is applied to hold a small portion of the live and beating heart muscle reasonably still and rigid for the short time required to insert the irrigation device. The soft elastomer layer on the underside of the applicator serves as a seal between the applicator tip and the muscle surface.

This procedure has the advantages that although an incision into the chest cavity is required, it is far smaller than that used for bypass surgery, and does not involve any severance of either the sternum or the rib cage. Further, life support systems are not needed whilst the irrigation device is being inserted, as the patient's heart is not closed down or stopped. As the incision is relatively short, the risk to the patient is minimized, the time required for the surgical procedure is minimized, and the patient's recovery time compared to bypass surgery significantly shortened. It is also contemplated that this procedure can be carried out using known robotic cardiovascular surgery devices.

It is also contemplated that the heart muscle stabilisation device will also find use on its own in invasive heart surgical procedures where the patient's rib cage has to be opened. A typical instance is in bypass surgery, where it is necessary to be able to stabilise the heart muscle temporarily during insertion of the bypass prosthesis.

Both the injection device and the applicator are each suitably made from any surgically acceptable material having adequate strength, and which can be adequately sterilized. Such materials are well known in the art. The irrigation device can be made as one unitary part, or from several parts. The two radial members must be adequately flexible, and a fibre reinforced elastomer material is therefore preferred. The hollow body portion can be fabricated from the same material, or it can be made from a more solid material. However, it should also be borne in mind that the irrigation device should be able to flex to some extent so as to accommodate movement of the heart muscle without causing damage to it. It would therefore appear that although fabrication of at least the hollow body portion from a metal such as a surgically acceptable stainless steel is possible, this might not be desirable as such a material may cause muscle damage. The irrigation device must be made from a material which will not be rejected by the body: suitable materials are well known in the art.

The head such as 4 in FIG. 1 presents a different problem. The material used must be capable of being made sharp enough at least at the tip to penetrate the heart muscle. It must also be flexible enough to allow the irrigation device to be ejected. A thin stainless steel assembly is preferred.

In the hollow body, the choice of aperture is quite wide: both perforations and slots are shown, but other methods can be used. The main requirement is to provide adequate blood flow without impairing the structural integrity of the hollow body. It is also contemplated that the irrigation device will be made in several lengths and diameters, to suit different heart muscles.

I claim:

1. A heart muscle wall stabilisation device comprising:
    a first, second and third hollow tubular member connected together into a Y-configuration by a hollow tubular adapter;
    the first member having a first end constructed and arranged to be connected to a surgically acceptable source of vacuum and including at least one hollow tubular flexible portion between the first end and the adapter;
    the second member having a first end attached to a first substantially planar hollow tip portion in communication therewith and including at least one hollow tubular flexible portion between the adapter and the first hollow tip portion;
    the third member having a first end attached to a second substantially planar hollow tip portion in communication therewith and including at least one hollow tubular flexible portion between the adapter and the second hollow tip portion; and
    both the first and the second hollow tip portion each including a foraminous underside, and a soft elastomeric layer attached to the underside of each tip portion which includes holes in communication with the foramens in the tip underside, and which provides a more or less planar surface for application to the heart muscle surface.

2. A heart muscle wall stabilisation device according to claim 1 wherein the first tubular member includes one hollow tubular flexible portion.

3. A heart muscle wall stabilisation device according to claim 1 wherein the first tubular member includes two hollow tubular flexible portions.

4. A heart muscle wall stabilisation device according to claim 1 wherein the first tubular member includes two hollow tubular flexible portions separated by bent portion.

5. A heart muscle stabilisation device according to claim 4 wherein the bent portion provides an angle of about 45°.

6. A heart muscle wall stabilisation device according to claim 1 wherein the second tubular member includes one hollow tubular flexible portion.

7. A heart muscle wall stabilisation device according to claim 1 wherein the third tubular member includes one hollow tubular flexible portion.

8. A heart muscle wall stabilisation device according to claim 1 wherein at least one of the connections between the first, second and third tubular members and the adapter are constructed and arranged to allow at least one of the tubular members to rotate relative to the adapter.

9. A heart muscle wall stabilisation device according to claim 8 wherein all of the connections between the first, second and third tubular members and the adapter are constructed and arranged to allow each of the first, second and third tubular members to rotate independently relative to the adapter.

10. A heart muscle wall stabilisation device according to claim 1 wherein at least one tip portion foraminous underside includes a first set of foramens communicating with a first space inside the hollow tip portion and a second set of foramens communicating with a second space inside the hollow tip portion; the soft elastomeric layer attached to the underside includes a first set of holes in communication with the first set of foramens and a second set of holes in communication with the second set of foramens, and the first, second and third tubular members together with the adapter are each constructed and arranged to provide vacuum independently to the at least one hollow tip portion having a first and a second internal space.

11. A heart muscle wall stabiliser according to claim 10 wherein one tip portion foraminous underside includes a first set of foramens communicating with a first space inside the hollow tip portion and a second set of foramens communicating with a second separate space inside the hollow tip portion; the soft elastomeric layer attached to the underside includes a first set of holes in communication with the first set of foramens and a second set of holes in communication with the second set of foramens, and the first, second and third tubular members together with the adapter are each constructed and arranged to provide vacuum independently to each of the first and second spaces in the one hollow tip portion including a first and a second internal space.

12. A heart muscle wall stabilisation device according to claim 1 wherein each tip portion foraminous underside of both the first tip portion and the second tip portion each separately include a first set of foramens communicating with a first space inside the hollow tip portion and a second set of foramens communicating with a second space inside the hollow tip portion; the first space and the second space are separated from each other; the soft elastomeric layer attached to the underside includes a first set of holes in communication with the first set of foramens and a second set of holes in communication with the second set of foramens, and the first, second and third tubular members together with the adapter are each constructed and arranged to provide vacuum independently to each of the first and second spaces in the at least one hollow tip portion.

13. A heart muscle wall stabilisation device according to claim 1 wherein the elastomeric layer includes soft elastomeric suction cups in communication with the foramens in the hollow tip portion underside.

14. A heart muscle wall stabilisation device according to claim 10 wherein the elastomeric layer includes a first set of soft elastomeric suction cups in communication with the first set of foramens and a second set of soft elastomeric suction cups in communication with the second set of foramens in the hollow tip portion underside.

15. A heart muscle wall stabilisation device according to claim 1 wherein the elastomeric layer includes soft elastomeric suction cups in communication with the foramens.

16. A heart muscle wall stabilisation device according to claim 10 wherein the elastomeric layer includes a first set of soft elastomeric suction cups in communication with the first set of foramens, and a second set of soft elastomeric suction cups in communication with the second set of foramens in the hollow tip portion underside.

17. A heart muscle wall stabilisation device according to claim 10 wherein the elastomeric layer includes a first set of soft elastomeric suction cups in communication with the first set of foramens, a second set of soft elastomeric suction cups in communication with the second set of foramens in the hollow tip portion underside, an elastomeric wall skirt portion surrounding the first and second set of elastomeric suction cups and the elastomeric layer, and a central elastomeric ridge wall joined to the elastomeric wall skirt and separating the first set of suction cups from the second set of suction cups and wherein the suction cups, the wall skirt, and the central ridge wall together provide a more or less planar surface for application to the heart muscle surface.

* * * * *